United States Patent [19]

Fujimura et al.

[11] Patent Number: 4,666,911
[45] Date of Patent: * May 19, 1987

[54] ALLOPHANOYLPIPERAZINE COMPOUND AND ANALGESIC COMPOSITION CONTAINING SAME AS ACTIVE INGREDIENT

[75] Inventors: Hajime Fujimura, Kyoto; Yasuzo Hiramatu, Otsu; Takahiro Yabuuchi, Takarazuka; Masakatu Hisaki, Hikone; Katsuo Takikawa, Naruto; Takaji Honna, Tokushima; Hidekazu Miyake, Tokushima; Makoto Kajitani, Tokushima, all of Japan

[73] Assignee: Taiho Pharmaceutical Company Limited, Tokyo, Japan

[*] Notice: The portion of the term of this patent subsequent to Jul. 14, 1998 has been disclaimed.

[21] Appl. No.: 281,343

[22] Filed: Jul. 8, 1981

[51] Int. Cl.[4] .................. A61K 31/495; C07D 295/10; C07D 295/16; C07D 295/14
[52] U.S. Cl. ..................... 514/255; 544/295; 544/370; 544/360; 544/377; 544/390; 544/392; 544/393; 544/358
[58] Field of Search ............... 544/400, 390, 384, 360, 544/295, 392, 370, 393, 377; 424/260; 564/38; 574/255

[56] References Cited

U.S. PATENT DOCUMENTS

| | | | |
|---|---|---|---|
| 3,251,737 | 5/1966 | Chubb et al. | 564/38 |
| 3,253,902 | 5/1966 | Munz et al. | 564/38 |
| 3,305,549 | 2/1967 | Chubb | 564/38 |
| 3,312,739 | 4/1967 | Thominet | 544/400 |
| 3,686,244 | 8/1972 | Marks | 564/38 |
| 4,278,672 | 7/1981 | Fujimara | 514/183 |
| 4,278,796 | 7/1981 | Corvi-Mora | 544/400 |
| 4,293,713 | 8/1981 | Fujimura et al. | 564/38 |
| 4,382,956 | 5/1983 | Kuhle et al. | 564/38 |

FOREIGN PATENT DOCUMENTS

| | | | |
|---|---|---|---|
| 2502684 | 7/1975 | Fed. Rep. of Germany | 424/250 |
| 7007821 | 12/1971 | France | 424/250 |
| 44-9387 | 4/1979 | Japan | 424/250 |
| 7208259 | 12/1972 | Netherlands | 424/250 |

OTHER PUBLICATIONS

Fujimura et al., "Pharmaceutical Composition . . . " Chem. Abst. 94:71501 (1980).
Turner, Robert, *Screening Methods in Pharmacology*, Academic Press, New York (1965), pp. 36-37.

*Primary Examiner*—Donald G. Daus
*Assistant Examiner*—G. Hendricks
*Attorney, Agent, or Firm*—Murray and Whisenhunt

[57] ABSTRACT

An analgesic compositon containing as active ingredient an allophanoylpiperazine compound represented by the general formula

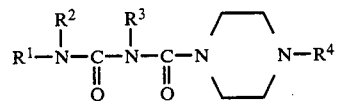

wherein $R^1$ represents a lower alkyl group or phenyl group; $R^2$ and $R^3$ each represents a hydrogen atom or a lower alkyl group; and $R^4$ represents a phenyl group or a substituted phenyl group having as substituent a halogen atom or methyl, trifluoromethyl, hydroxyl, methoxy, methylenedioxy, nitro, or carboxyl group; pyridyl group, pyrimidyl group, thiazolyl group, benzyl group, cinnamyl group, cyclohexyl group, a lower alkyl group, a substituted lower alkyl group having chlorine atom or hydroxyl group as substituent; or a lower alkenyl group.

22 Claims, No Drawings

ALLOPHANOYLPIPERAZINE COMPOUND AND ANALGESIC COMPOSITION CONTAINING SAME AS ACTIVE INGREDIENT

This invention relates to a novel allophanoylpiperazine compound and to an analgesic composition containing same as active ingredient.

The allophanoylpiperazine compound of this invention is represented by the general formula

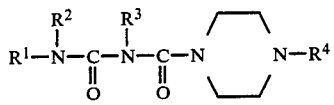

(1)

wherein $R^1$ represents a lower alkyl group or phenyl group; $R^2$ and $R^3$ each represents a hydrogen atom or a lower alkyl group; and $R^4$ represents phenyl group or a substituted phenyl group having as substituent a halogen atom or methyl, trifluoromethyl, hydroxyl, methoxy, methylenedioxy, nitro, or carboxyl group; pyridyl group, pyrimidyl group, thiazolyl group, benzyl group, cinnamyl group, cyclohexyl group, a lower alkyl group, a substituted lower alkyl group having chlorine atom or hydroxyl group as substituent; or a lower alkenyl group.

The compound of this invention is a novel compound not described in the literature and not only has an analgesic activity and is useful as an analgesic but also has an anti-inflammatory activity.

There has heretofore been published entirely no report on the compound having a skeleton represented by the formula

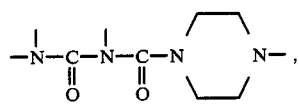

not to mention the allophanoylpiperazine compound represented by the formula (1). The present inventors carried out extensive studies on the above-said types of allophanoylpiperazine compounds, aiming at the development of a compound having an analgesic activity. It was found, as a result, that the compound represented by the general formula (1) answers the purpose. This finding has led to the accomplishment of this invention.

The allophanoylpiperazine compound of this invention is prepared by one of the methods exemplified below.:

Method A

This method is characterized by reacting an allophanoyl chloride represented by the general formula (2) with a piperazine represented by the general formula (3) according to the following reaction scheme:

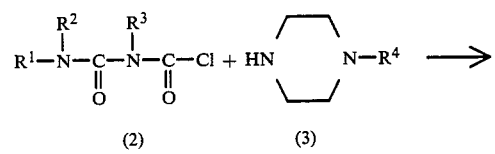

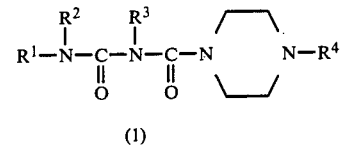

(1)

The reaction of allophanoyl chloride (2) and piperazine (3) according to the above scheme is carried out generally in a solvent. Although any solvent which does not participate in the reaction can be used, generally preferred are ethers such as ethyl ether, dioxane, and tetrahydrofuran, halogenated hydrocarbons such as methylene chloride, chloroform, and carbon tetrachloride, and aromatic hydrocarbons such as benzene, toluene, and xylenes. If necessary for the reaction, suitable condensation promoters such as basic compounds, e.g. trialkylamines and pyridine, may be used. An advantageous molar ratio of allophanoyl chloride (2) to piperazine (3) is generally in the range of from 1 to 2, though other ratios may be selected to suit the particular case. The reaction temperature can also be selected suitably, but the reaction generally proceeds advantageously at a temperature in the range of from $-20°$ to $50°$ C.

Method B

This method is characterized by reacting an isocyanate represented by the general formula (4) with a carbamoyl piperazine compound represented by the general formula (5) according to the following reaction scheme. This method, however, is applicable only to the case where $R^2$ in the formula (1) is hydrogen atom.

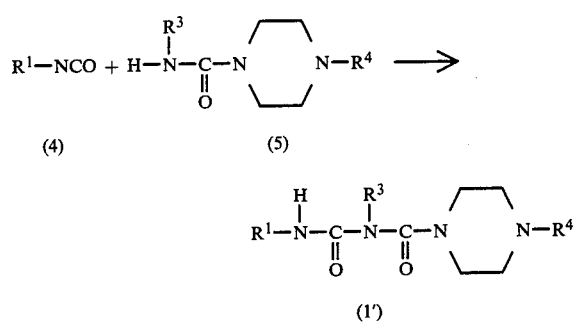

The reaction of isocyanate (4) and carbamoylpiperazine compound (5) is carried out generally in a solvent in the presence of a catalyst. Suitable catalysts are Lewis acids such as anhydrous aluminum chloride, anhydrous stannic chloride, and titanium tetrachloride. Although any solvent not participating in the reaction can be used, generally suitable are halogenated hydrocarbons such as methylene chloride, chloroform and carbon tetrachloride and aromatic hydrocarbons such as benzene, toluene and xylenes. Although the ratios among the isocyanate (4), carbamoyl piperazine compound (5) and catalyst can be suitably selected, it is advantageous to use the reactants in approximately equimolar amounts. The reaction temperature can also be suitably selected, but the reaction generally proceeds advantageously at a temperature from $-20°$ C. to room temperature.

Method C

This method is characterized by reacting an allophanoylpiperazine represented by the general formula (6) with a halogen compound represented by the general formula (7) [wherein X represents a halogen atom and $R^5$ is pyridyl group, pyrimidyl group, thiazolyl group, benzyl group, cinnamyl group, cyclohexyl group, a lower alkyl group, a substituted lower alkyl group, having chlorine atom(s) or hydroxy group(s) as the substituent(s)] according to the following reaction scheme. This method, however, is not applicable to the case where $R^4$ in the general formula is phenyl or a substituted phenyl group.

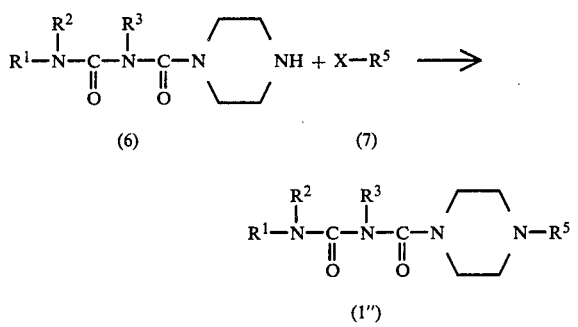

The reaction between the allophanoylpiperazine (6) and the halogen compound (7) according to the above scheme is carried out generally in a solvent in the presence of a basic compound such as, for example, a trialkylamine, pyridine, or an alkali carbonate. Solvents which are generally used are lower alcohols such as methanol, ethanol and propanol, halogenated hydrocarbons such as methylene chloride, chloroform and carbon tetrachloride, and aromatic hydrocarbons such as benzene, toluene and xylenes, though any other solvent not participating in the reaction can be used. Although the ratios among the allophanoylpiperazine (6), halogen compound (7) and basic compound can be suitably selected, it is advantageous for the reaction to use these reactants in equimolar amounts. The reaction temperature can also be selected suitably, but the reaction generally proceeds advantageously at a temperature from $-20°$ C. to the boiling point of the solvent.

The allophanoylpiperazine (6) used as a reactant in the above reaction is a novel compound which is easily prepared by converting the starting material 1-formylpiperazine (8) to a compound of the general formula (9) by the above-mentioned method A or B, and deformylating the compound (9) by the known method [Yakugaku Zasshi (Journal of the Pharmaceutical Society of Japan), 74, 1049-1052 (1954)].

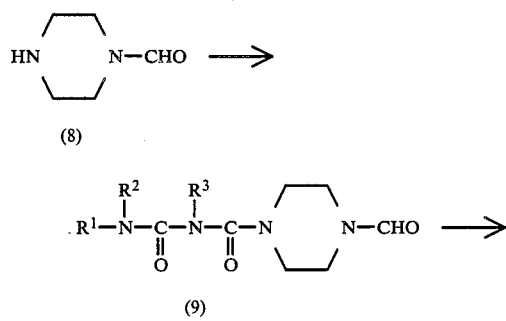

-continued

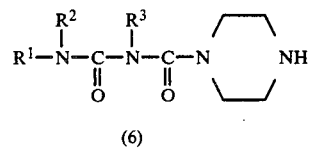

The allophanoylpiperazine compound (1) formed by the methods A, B and C can be easily isolated by the common means of separation.

The daily dose of the present analgesic is 0.5 to 1,000 mg, preferably 1 to 500 mg in terms of the allophanoylpiperazine compound of general formula (1) for adult, which is administered in 1 to 4 single doses. The dosage in particular cases should be suitably adjusted depending on the clinical features and age of the patient. It is administered in various forms such as oral preparation, injection, suppository for rectal application, and external preparation.

The analgesic of this invention is prescribed for medical application as a composition containing excipients generally used in the art such as, for example, calcium carbonate, calcium phosphate, starch, sucrose, lactose, talc, magnesium stearate, gelatin, polyvinylpyrrolidone, gum arabic, sorbit, microcrystalline cellulose, polyethylene glycol, carboxymethylcellulose, silica, polyvinylacetal diethylaminoacetate, hydroxypropylmethylcellulose, and shellac. Tablets may be coated by the technique well known to the art.

The liquid preparations for oral administration include suspensions, solutions, sirups, elixirs in water or oil, which are dispensed in the generally known manner.

Injections are suspensions or solutions in water or oil, or filled powders or lyophilized powders which are to be dissolved before use. The injections are prepared in the customary manner.

For rectal application, the present analgesic is offered as a suppository composition which may contain those pharmaceutical excipients which are well known to the art, such as, for example, polyethylene glycol, lanolin, cacao butter, and fatty acid triglycerides.

The external preparation is applied preferably in the form of ointment or cream prepared by incorporating the active ingredient of this invention in an ointment base or the like in the customary manner.

The invention is illustrated below in detail with reference to examples of the synthesis of allophanoylpiperazine compounds represented by the general formula (1), results of tests for the analgesic activity of the compounds thus obtained, and examples of pharmaceutical preparations containing same.

Examples of synthesis of allophanoylpiperazine compounds of the general formula (1) by the methods A, B and C are as described below. Characteristics of the compounds obtained in these Examples and in other experiments conducted in a manner similar to that in these Examples are as shown in Table 1.

EXAMPLES OF SYNTHESIS BY METHOD A

Example 1

(synthesis of the compound No. 6 in Table 1)

Into 40 ml of dichloromethane, was dissolved 6.5 g of 1-phenylpiperazine. To the solution, while being stirred and cooled in ice, was added dropwise 3.0 g of 2,4-dimethylallophanoyl chloride. After 0.5 hour of reaction at room temperature, the reaction mixture was washed with water and dried over anhydrous sodium sulfate. The solvent was removed by distillation and the residue was recrystallized from a mixture of ethanol and petroleum ether to obtain 4.0 g (72% yield) of 1-(2,4-dimethyl-allophanoyl)-4-phenylpiperazine having a melting point of 79°–80° C.

Example 2

(synthesis of compound No. 19 in Table 1)

Into 80 ml of dichloromethane, were dissolved 10.8 g of 1-(p-fluorophenyl)piperazine and 6.1 g of triethylamine. To the solution, while being stirred and cooled in ice, was added dropwise 10.0 g of 2,4,4-trimethylallophanoyl chloride. After one hour of reaction at room temperature, the reaction mixture was washed with water and dried over anhydrous sodium sulfate. The solvent was removed by distillation and the residue was recrystallized from a mixture of ethanol and ether to obtain 13.7 g (74% yield) of 1-(p-fluorophenyl)-4-(2,4,4-trimethylallophanoyl)piperazine having a melting point of 83°–84° C.

EXAMPLES OF SYNTHESIS BY METHOD B

Example 3

(synthesis of compound No. 1 in Table 1)

Into 70 ml of dichloromethane, were dissolved 4.1 g of 4-phenylpiperazine-1-carboxamide and 1.2 g of methyl isocyanate. To the solution, while being stirred and cooled in ice, was added dropwise 5.2 g of stannic chloride. After 15 hours of reaction at room temperature, water was added to separate an organic layer. The organic layer was dried over anhydrous sodium sulfate and freed from the solvent by distillation. The residue was recrystallized from ethanol to obtain 2.7 g (51% yield) of 1-(4-methylallophanoyl)-4-phenylpiperazine having a melting point of 198°–200° C.

Example 4

(synthesis of compound No. 12 in Table 1)

Into 70 ml of dichloromethane, was dissolved 4.3 g of 1-(methylcarbamoyl)-4-(m-trifluoromethylphenyl)piperazine and 0.9 g of methyl isocyanate. To the solution, while being stirred and cooled in ice, was added dropwise 3.9 g of anhydrous stannic chloride. After 15 hours of reaction at room temperature, the precipitated matter was collected by filtration and stirred in a mixture of dichloromethane and water. The organic layer was separated and dried over anhydrous sodium sulfate. After removal of the solvent by distillation, the residue was recrystallized from a mixture of ethanol and petroleum ether to obtain 3.2 g (62% yield) of 1-(2,4-dimethylallophanoyl)-4-(m-trifluoromethylphenyl)piperazine.

EXAMPLE OF SYNTHESIS BY METHOD C

Example 5

(synthesis of compound No. 44 in Table 1)

To 20 ml of ethanol, were added 5.0 g of 1-(2,4,4-trimethylallophanoyl)piperazine hydrochloride and 3.7 g of sodium carbonate. To the resulting mixture, was added dropwise with stirring 2.5 g of isopropyl bromide. The mixture was allowed to react under reflux for 8 hours and the precipitate was removed by filtration. The filtrate was concentrated and the residue was purified with a silica gel column to obtain an oil. This oil was converted to hydrochloride in the customary way and recrystallized from ethanol to obtain 3.8 g (65% yield) of 1-(isopropyl)-4-(2,4,4-trimethylallophanoyl)-piperazine hydrochloride having a melting point of 213°–215° C.

The 1-(2,4,4-trimethylallophanoyl)piperazine hydrochloride used in the above Example was synthesized as described below.

Into 600 ml of tetrahydrofuran, were dissolved 41 g of 1-formylpiperazine and 54.5 g of triethylamine. To the solution, while being stirred and cooled in ice, was added dropwise 56 g of 2,4,4-trimethylallophanyl chloride. The mixture was allowed to react at room temperature for 6 hours and the precipitate was removed by filtration. The filtrate was concentrated and the residue was recrystallized from tetrahydrofuran to obtain 41 g of 1-formyl-4-(2,4,4-trimethylallophanoyl)piperazine. This compound was mixed with 800 ml of 6N hydrochloric acid and the mixture was heated with stirring at 60° C. for one hour. The reaction mixture was concentrated and the residue was recrystallized from ethanol to obtain 35.2 g of 1-(2,4,4-trimethylallophanoyl)piperazine hydrochloride having a melting point of 215° C.

| Elementary analysis: ($C_9H_{18}N_4O_2 \cdot HCl$) | | |
|---|---|---|
| C % | H % | N % |
| Calculated 43.11 | 7.64 | 22.35 |
| Found 42.92 | 7.90 | 22.11 |

TABLE 1

$$R^1-N(R^2)-C(=O)-N(R^3)-C(=O)-N\text{(piperazine)}N-R^4$$

| Compound No. | $R^1$ | $R^2$ | $R^3$ | $R^4$ | Method of synthesis | Melting point (°C.) | Molecular formula | Elementary analysis (%) Calculated (found) | | |
|---|---|---|---|---|---|---|---|---|---|---|
| | | | | | | | | C | H | N |
| 1 | —CH₃ | —H | —H | phenyl | B | 198–200 | C₁₃H₁₈N₄O₂ | 59.53 (59.43) | 6.92 (7.15) | 21.36 (21.27) |
| 2 | " | " | " | 2-methylphenyl | B | 177–178 | C₁₄H₂₀N₄O₂ | 60.85 (60.74) | 7.30 (7.20) | 20.28 (20.35) |
| 3 | " | " | " | 3-methylphenyl | B | 156–157 | C₁₄H₂₀N₄O₂ | 60.85 (60.95) | 7.30 (7.30) | 20.28 (20.35) |
| 4 | " | " | " | 4-methylphenyl | B | 208–209 | C₁₄H₂₀N₄O₂ | 60.85 (60.75) | 7.30 (7.28) | 20.28 (20.19) |
| 5 | " | " | " | 3-trifluoromethylphenyl | B | 160–161 | C₁₄H₁₇F₃N₄O₂ | 50.91 (50.89) | 5.19 (5.21) | 16.96 (16.84) |
| 6 | " | " | —CH₃ | phenyl | A | 79–80 | C₁₄H₂₀N₄O₂ | 60.85 (60.83) | 7.30 (7.49) | 20.28 (20.16) |
| 7 | " | " | " | 2-chlorophenyl | A | 118–119 | C₁₄H₁₉ClN₄O₂ | 54.11 (54.14) | 6.16 (6.12) | 18.03 (17.90) |

TABLE 1-continued $$R^1-N(R^2)-C(=O)-N(R^3)-C(=O)-N\underset{\underset{N-R^4}{\diagdown}}{\diagup}$$

| Compound No. | R¹ | R² | R³ | R⁴ | Method of synthesis | Melting point (°C.) | Molecular formula | Elementary analysis (%) Calculated (found) | | |
|---|---|---|---|---|---|---|---|---|---|---|
| | | | | | | | | C | H | N |
| 8 | " | " | " | 3-Cl-phenyl | A | 114–115 | $C_{14}H_{19}ClN_4O_2$ | 54.11 (53.84) | 6.16 (6.37) | 18.03 (17.85) |
| 9 | " | " | " | 4-Cl-phenyl | A | 120–121 | $C_{14}H_{19}ClN_4O_2$ | 54.11 (53.99) | 6.16 (5.96) | 18.03 (17.99) |
| 10 | " | " | " | 4-CH₃-phenyl | B | 111–112 | $C_{15}H_{22}N_4O_2$ | 62.05 (62.05) | 7.64 (7.67) | 19.30 (19.05) |
| 11 | " | " | " | 4-OCH₃-phenyl | A | 122–123 | $C_{15}H_{22}N_4O_3$ | 58.81 (58.65) | 7.24 (7.22) | 18.29 (18.08) |
| 12 | " | " | " | 3-CF₃-phenyl | B | 97–98 | $C_{15}H_{19}F_3N_4O_2$ | 52.32 (52.10) | 5.56 (5.78) | 16.27 (16.08) |
| 13 | " | " | " | —CH₂-phenyl | A | 67–69 | $C_{15}H_{22}N_4O_2$ | 62.05 (61.76) | 7.64 (7.67) | 19.30 (19.12) |
| 14 | " | —CH₃ | " | phenyl | A | 210–100 | $C_{15}H_{22}N_4O_2 \cdot HCl$ | 55.12 (54.81) | 7.09 (6.97) | 17.14 (16.98) |

TABLE 1-continued
$$R^1-N(R^2)-C(O)-N(R^3)-C(O)-N\text{-piperazine-}N-R^4$$
| Compound No. | R¹ | R² | R³ | R⁴ | Method of synthesis | Melting point (°C.) | Molecular formula | Elementary analysis (%) Calculated (found) | | |
|---|---|---|---|---|---|---|---|---|---|---|
| | | | | | | | | C | H | N |
| 15 | " | " | " | 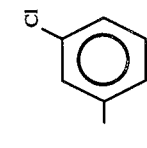 2-Cl-C₆H₄ | A | 98–100 | $C_{15}H_{21}ClN_4O_2$ | 55.47 (55.38) | 6.52 (6.77) | 17.25 (17.02) |
| 16 | " | " | " | 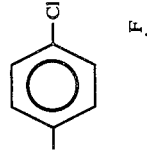 3-Cl-C₆H₄ | A | 95–96 | $C_{15}H_{21}ClN_4O_2$ | 55.47 (55.26) | 6.52 (6.70) | 17.25 (17.07) |
| 17 | " | " | " | 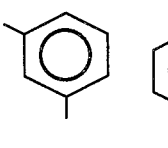 4-Cl-C₆H₄ | A | 102–104 | $C_{15}H_{21}ClN_4O_2$ | 55.47 (55.37) | 6.52 (6.36) | 17.25 (17.15) |
| 18 | " | " | " | 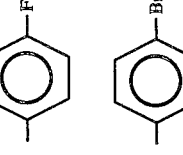 3-F-C₆H₄ | A | 76–77 | $C_{15}H_{21}FN_4O_2$ | 58.43 (58.55) | 6.86 (6.78) | 18.17 (18.31) |
| 19 | " | " | " | 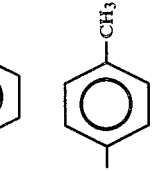 4-F-C₆H₄ | A | 83–84 | $C_{15}H_{21}FN_4O_2$ | 58.43 (58.60) | 6.86 (7.09) | 18.17 (18.13) |
| 20 | " | " | " |  4-Br-C₆H₄ | A | 91–93 | $C_{15}H_{21}BrN_4O_2$ | 48.79 (48.66) | 5.73 (5.76) | 15.17 (15.16) |
| 21 | " | " | " | 4-CH₃-C₆H₄ | A | 106–107 | $C_{16}H_{24}N_4O_2$ | 63.13 (63.03) | 7.95 (7.82) | 17.49 (17.22) |

TABLE 1-continued $$R^1-N(R^2)-\underset{\underset{O}{\|}}{C}-N(R^3)-\underset{\underset{O}{\|}}{C}-N\overbrace{\phantom{XXX}}^{}N-R^4$$

| Compound No. | R¹ | R² | R³ | R⁴ | Method of synthesis | Melting point (°C.) | Molecular formula | Elementary analysis (%) Calculated (found) | | |
|---|---|---|---|---|---|---|---|---|---|---|
| | | | | | | | | C | H | N |
| 22 | " | " | " | 3-CF₃-C₆H₄ | A | 98–100 | C₁₆H₂₁F₃N₄O₂ | 53.63 (53.57) | 5.91 (5.88) | 15.63 (15.61) |
| 23 | " | " | " | 4-CF₃-C₆H₄ | A | 78–80 | C₁₆H₂₁F₃N₄O₂ | 53.63 (53.64) | 5.91 (6.05) | 15.63 (15.71) |
| 24 | " | " | " | 3-OCH₃-C₆H₄ | A | 102–104 | C₁₆H₂₄N₄O₃ | 59.98 (60.06) | 7.55 (7.28) | 17.49 (17.46) |
| 25 | " | " | " | 4-OCH₃-C₆H₄ | A | 101–103 | C₁₆H₂₄N₄O₃ | 59.98 (59.79) | 7.55 (7.73) | 17.49 (17.22) |
| 26 | " | " | " | 3-OH-C₆H₄ | A | 144–145 | C₁₅H₂₂N₄O₃ | 58.81 (58.77) | 7.24 (7.40) | 18.29 (18.49) |
| 27 | " | " | " | 4-OH-C₆H₄ | A | 175–177 | C₁₅H₂₂N₄O₃ | 58.81 (59.05) | 7.24 (7.36) | 18.29 (18.13) |
| 28 | " | " | " | 3-NO₂-C₆H₄ | A | 132–134 | C₁₅H₂₁N₅O₄ | 53.72 (53.96) | 6.31 (6.68) | 20.88 (20.77) |

TABLE 1-continued $R^1-N(R^2)-C(=O)-N(R^3)-C(=O)-N(\text{piperazine})-R^4$

| Compound No. | R¹ | R² | R³ | R⁴ | Method of synthesis | Melting point (°C.) | Molecular formula | Elementary analysis (%) Calculated (found) C | H | N |
|---|---|---|---|---|---|---|---|---|---|---|
| 29 | " | " | " | 4-COOH-C₆H₄ | A | 203–205 | $C_{16}H_{22}N_4O_2 \cdot \tfrac{1}{2}H_2O$ | 56.71 (56.75) | 6.69 (6.83) | 16.53 (16.52) |
| 30 | " | " | " | 3,4-Cl₂-C₆H₃ | A | 81–83 | $C_{15}H_{20}Cl_2N_4O_2$ | 50.15 (50.09) | 5.61 (5.65) | 15.60 (15.58) |
| 31 | " | " | " | 3,5-Cl₂-C₆H₃ | A | 108–110 | $C_{15}H_{20}Cl_2N_4O_2 \cdot HCl$ | 45.53 (45.70) | 5.35 (5.22) | 14.16 (14.14) |
| 32 | " | " | " | 2-Cl-4-OH-C₆H₃ | A | 225–227 | $C_{15}H_{21}ClN_4O_3$ | 52.86 (52.81) | 6.21 (6.23) | 16.44 (16.21) |
| 33 | " | " | " | 2-CF₃-4-OH-C₆H₃ | A | 193–195 | $C_{16}H_{21}F_3N_4O_3$ | 51.33 (51.77) | 5.65 (5.90) | 14.97 (14.93) |
| 34 | " | " | " | 2-CF₃-4-Cl-C₆H₃ | A | 110–112 | $C_{16}H_{19}ClF_3N_4O_2 \cdot HCl$ | 44.77 (44.76) | 4.93 (5.09) | 13.05 (12.93) |

TABLE 1-continued

R¹—N(R²)—C(=O)—N(R³)—C(=O)—N(piperidine)—R⁴

| Compound No. | R¹ | R² | R³ | R⁴ | Method of synthesis | Melting point (°C.) | Molecular formula | Elementary analysis (%) Calculated (found) | | |
|---|---|---|---|---|---|---|---|---|---|---|
| | | | | | | | | C | H | N |
| 35 | " | " | " |  2-OCH₃, 4-OCH₃-phenyl | A | 177–180 | $C_{17}H_{20}N_4O_4 \cdot HCl$ | 52.78 (52.54) | 7.03 (7.22) | 14.48 (14.26) |
| 36 | " | " | " | 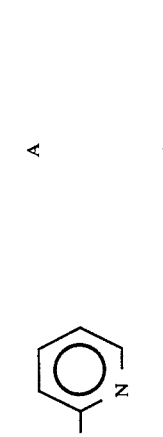 methylenedioxyphenyl | A | 136–137 | $C_{16}H_{22}N_4O_4$ | 57.47 (57.28) | 6.63 (6.89) | 16.76 (16.54) |
| 37 | " | " | " |  pyridyl | A | 108–109 | $C_{14}H_{21}N_5O_2$ | 57.71 (57.75) | 7.27 (7.17) | 24.04 (23.90) |
| 38 | " | " | " | 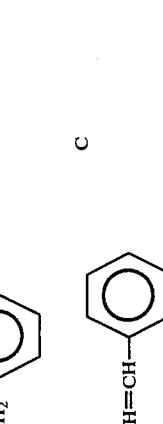 pyridyl | A | 166–167 | $C_{13}H_{20}N_6O_2$ | 53.41 (53.37) | 6.90 (7.10) | 28.75 (28.41) |
| 39 | " | " | " | 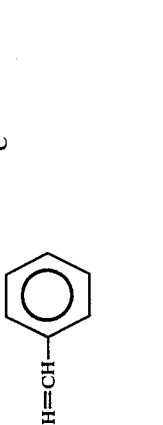 methylthiazolyl | A | 159–161 | $C_{12}H_{19}N_5O_2S$ | 48.47 (48.84) | 6.44 (6.88) | 23.55 (23.51) |
| 40 | " | " | " | —CH₂— | A | 95–97 | $C_{16}H_{24}N_4O_2$ | 63.13 (62.98) | 7.95 (8.31) | 18.41 (18.18) |
| 41 | " | " | " | —CH₂CH=CH—phenyl | C | 208–210 | $C_{16}H_{26}N_4O_2 \cdot HCl$ | 58.93 (58.92) | 7.42 (7.53) | 15.27 (15.28) |

TABLE 1-continued $$R^1-\underset{\underset{O}{\parallel}}{N}-\underset{R^2}{\overset{R^2}{C}}-\underset{\underset{O}{\parallel}}{N}-\underset{R^3}{\overset{R^3}{C}}-N\underset{}{\diagdown}\text{piperazine}\diagup N-R^4$$

| Compound No. | $R^1$ | $R^2$ | $R^3$ | $R^4$ | Method of synthesis | Melting point (°C.) | Molecular formula | Elementary analysis (%) Calculated (found) C | H | N |
|---|---|---|---|---|---|---|---|---|---|---|
| 42 | " | " | " | cyclohexyl | A | 212–214 | $C_{15}H_{26}N_4O_2 \cdot HCl$ | 54.12 (53.99) | 8.78 (8.84) | 16.83 (16.87) |
| 43 | " | " | " | —$CH_3$ | A | 189–191 | $C_{10}H_{20}N_4O_2 \cdot HCl$ | 45.36 (45.46) | 7.99 (8.07) | 21.16 (21.06) |
| 44 | " | " | " | —$CH(CH_3)_2$ | C | 213–215 | $C_{12}H_{24}N_4O_2 \cdot HCl$ | 49.22 (48.95) | 8.61 (9.05) | 19.14 (19.09) |
| 45 | " | " | " | —$(CH_2)_3CH_3$ | C | 191–193 | $C_{13}H_{26}N_4O_2 \cdot HCl$ | 50.89 (50.54) | 8.87 (9.20) | 18.26 (18.16) |
| 46 | " | " | " | —$CH_2CH=C(CH_3)_2$ | C | 199–200 | $C_{14}H_{26}N_4O_2 \cdot HCl$ | 52.74 (52.33) | 8.53 (8.63) | 17.57 (17.30) |
| 47 | " | " | " | —$CH_2CH_2OH$ | A | 159–161 | $C_{11}H_{22}N_4O_3 \cdot HCl$ | 44.82 (44.73) | 7.86 (8.04) | 19.01 (19.05) |
| 48 | " | " | " | —$CH_2CH_2Cl$ | A | 156–158 | $C_{11}H_{21}ClN_4O_2 \cdot HCl$ | 42.18 (42.20) | 7.08 (7.05) | 17.89 (17.63) |
| 49 | phenyl | —H | —H | —$CH_3$ | B | 184–187 | $C_{13}H_{15}N_4O_2$ | 59.93 (59.31) | 6.92 (7.08) | 21.36 (21.27) |
| 50 | " | " | —$CH_3$ | 3-CF$_3$-phenyl | A | 119–120 | $C_{20}H_{21}FN_4O_2$ | 59.11 (58.91) | 5.21 (5.26) | 13.79 (13.82) |

Pharmacological test.

The methods for testing the analgesic activity and the acute toxicity are as described below and the test results were as shown in Table 2.

Analgesic activity:

1. Acetic acid-induced stretching method:

According to the method of Koster et al. [Fed. Pro., 18, 412 (1959)], ddy strain male mice (each 20 to 25 g in body weight) were used for the test. One hour after the oral administration of 100 mg/kg of the test drug, 0.35 ml of a 0.6% acetic acid solution was administered intraperitoneally to each mouse to observe the stretching symptom and calculate the inhibitory ratio (in %). In Table 2, figures marked with an asterisk (*) are median effective doses, $ED_{50}$ (mg/kg), and NT stands for "not tested."

2. Haffner method:

The test was performed by the modified method of Fujimura et al [Bulletin of the Institute for Chemical Research, Kyoto University, 25, 36 (1951)] using ddy strain male mice (each 20 to 25 g in body weight). Thirty miutes after the oral administration of 100 mg/kg of the drug under test, a threshold dose (2.5 mg/kg) of morphine hydrochloride was subcutaneously administered. The pain reaction of the mouse caused by clamping was observed for one hour to determine the inhibitory ratio (in %). In Table 2, figures marked with an asterisk (*) are median effective doses, $ED_{50}$ (mg/kg), and NT stands for "not tested."

Acute toxicity:

The acute toxicity test was performed by using ddy strain male mice (each 20 to 25 g in body weight). Each mouse was observed for general symptoms for a week after oral administration of the test drug. The dose (mg/kg) and the corresponding ratio, (number of dead animals)/(number of test animals in one group), were as shown in Table 2, wherein the figures marked with an asterisk (*) are median lethal doses, $LD_{50}$ (mg/kg).

In the above tests, drugs were used as a solution or suspension in a 0.1–0.25% carboxymethylcellulose solution.

TABLE 2

| Compound No. | Acute toxicity | Analgesic activity (%) | |
|---|---|---|---|
| | | Acetic acid stretching method | Haffner method |
| 1 | 2000 - 0/4 | 75 | 25 |
| 2 | 2000 - 0/4 | 37.5 | 25 |
| 3 | 2000 - 0/4 | 75 | 37.5 |
| 4 | 2000 - 0/4 | 37.5 | 62.5 |
| 5 | 2000 - 0/4 | 50 | 25 |
| 6 | 1000 - 0/4 2000 - 4/4 | 62.5 | 50 |
| 7 | 1000 - 0/4 2000 - 4/4 | 75 | 25 |
| 8 | 1000 - 0/4 2000 - 1/4 | 75 | 37.5 |
| 9 | 1000 - 2/4 2000 - 3/4 | 87.5 | 50 |
| 10 | 2000 - 1/4 | 75 | 50 |
| 11 | 1000 - 0/4 2000 - 1/4 | NT | 37.5 |
| 12 | 500 - 0/4 1000 - 4/4 | *8.0 | 75 |
| 13 | 1000 - 0/4 2000 - 1/4 | 37.5 | 50 |
| 14 | 500 - 1/4 1000 - 4/4 | *39 | *20 |
| 15 | 500 - 1/4 1000 - 4/4 | 100 | 50 |
| 16 | 500 - 2/4 1000 - 4/4 | 100 | 62.5 |

TABLE 2-continued

| Compound No. | Acute toxicity | Analgesic activity (%) | |
|---|---|---|---|
| | | Acetic acid stretching method | Haffner method |
| 17 | *546 | *2.1 | *15.1 |
| 18 | *500 | *2.5 | *30 |
| 19 | *660 | *3.0 | *26 |
| 20 | *432 | *1.0 | *6.2 |
| 21 | 1000 - 3/4 | 87.5 | 50 |
| 22 | *715 | *2.2 | *8.2 |
| 23 | *281 | *11 | 60 |
| 24 | *1012 | *8.0 | 60 |
| 25 | 500 - 0/4 1000 - 4/4 | 25 | 62.5 |
| 26 | 2000 - 0/4 | 37.5 | NT |
| 27 | 2000 - 0/4 | 37.5 | NT |
| 28 | 500 - 1/6 1000 - 6/6 | *30 | *30 |
| 29 | 1000 - 0/6 2000 - 1/6 | *60 | *40 |
| 30 | 500 - 3/6 1000 - 6/6 | *15 | *15 |
| 31 | 500 - 0/6 1000 - 2/6 | *61.5 | NT |
| 32 | 2000 - 0/4 | 37.5 | NT |
| 33 | 2000 - 0/4 | 37.5 | NT |
| 34 | 250 - 0/6 500 - 2/6 | *14.6 | *13.3 |
| 35 | 1000 - 0/4 2000 - 4/4 | *25 | NT |
| 36 | 500 - 0/4 1000 - 4/4 | *28 | 80 |
| 37 | 1000 - 1/4 2000 - 4/4 | 50 | 25 |
| 38 | 500 - 0/4 1000 - 4/4 | 25 | 12.5 |
| 39 | 1000 - 0/4 2000 - 4/4 | 62.5 | 50 |
| 40 | 500 - 0/4 1000 - 4/4 | 50 | 37.5 |
| 41 | 500 - 0/4 1000 - 4/4 | 25 | 25 |
| 42 | 1000 - 3/4 | *91 | *64 |
| 43 | 2000 - 0/4 | *74 | *60 |
| 44 | 2000 - 0/4 | 75 | 50 |
| 45 | 2000 - 0/4 | 37.5 | 37.5 |
| 46 | 1000 - 0/4 2000 - 3/4 | 50 | 37.5 |
| 47 | 2000 - 0/4 | *82 | *103 |
| 48 | 500 - 4/4 | NT | *62 |
| 49 | 500 - 0/4 1000 - 2/4 | 50 | NT |
| 50 | 1000 - 0/4 | 25 | 37.5 |
| Amino-pyrine | *792 | *45 | 60 |
| Phenyl-butazone | *689 | *120 | 37.5 |

In conclusion, some examples of pharmaceutical preparations contaning the allophanylpiperazine compounds of this invention are given below.

PREPARATION EXAMPLE 1

Granules are prepared in the customary way according to the following recipe:

| | mg |
|---|---|
| 1-(3-Trifluoromethylphenyl)-4-(2,4,4-trimethylallophanoyl)piperazine (compound No. 22) | 5 |
| Lactose | 695 |
| Cornstarch | 280 |
| Hydroxypropylcellulose | 20 |
| Per fold | 1,000 |

PREPARATION EXAMPLE 2

Tablets are prepared in the customary way according to the following receipe:

| | mg |
|---|---|
| 1-(4-Chlorophenyl)-4-(2,4,4-trimethyl-allophanoyl)piperazine (compound No. 17) | 10 |
| Lactose | 85 |
| Crystalline cellulose | 50 |
| Hydroxypropylstarch | 30 |
| Talc | 4 |
| Magnesium stearate | 1 |
| Per tablet | 180 |

PREPARATION EXAMPLE 3

Capsules are prepared in the customary way according to the following recipe:

| | mg |
|---|---|
| 1-(3-Nitrophenyl)-4-(2,4,4-trimethyl-allophanoyl)piperazine (compound No. 28) | 100 |
| Lactose | 50 |
| Potato starch | 50 |
| Crystalline cellulose | 109 |
| Magnesium stearate | 1 |
| Per capsule | 400 |

PREPARATION EXAMPLE 4

Suppository is prepared in the customary manner according to the following recipe:

| | mg |
|---|---|
| 1-(3-Trifluoromethylphenyl)-4-(2,4,4-trimethylallophanoyl)-piperazine (compound No. 22) | 10 |
| Witepzol W-35 (trademark for Dynamit Nobel Co.) | 990 |
| Per piece | 1,000 |

PREPARATION EXAMPLE 5

An injection is prepared in the customary manner according to the following recipe:

| | mg |
|---|---|
| 1-(2,4,4-Trimethylallophanoyl)-4-phenylpiperazine (compound No. 14) | 5 |
| Sodium chloride | 18 |
| Distilled water for injection to make up to | 2 ml/ampule |

PREPARATION EXAMPLE 6

An ointment is prepared in the customary manner according to the following recipe:

| | g |
|---|---|
| 1-(3,4-Dichlorophenyl)-4-(2,4,4-trimethylallophanoyl)piperazine (compound No. 30) | 2.0 |
| White petrolatum | 23.0 |
| Stearyl alcohol | 22.0 |
| Propylene glycol | 12.0 |
| Sodium lauryl sulfate | 1.5 |
| Ethyl p-hydroxybenzoate | 0.025 |
| Propyl p-hydroxybenzoate | 0.015 |
| Purified water to make up to | 100 |

What is claimed is:

1. An allophanylpiperazine compound represented by the general formula

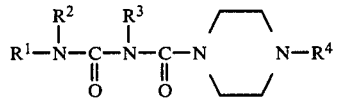

wherein $R^1$ represents a lower alkyl group or phenyl group; $R^2$ represents a lower alkyl group; $R^3$ represents a lower alkyl group; and $R^4$ represents phenyl group or a substituted phenyl group having as substituent a halogen atom or methyl, trifluoromethyl, hydroxy, methoxy, methylenedioxy, nitro or carbonyl group; pyridyl group, pyrimidyl group, thiazolyl group, benzyl group, cinnamyl group, cyclohexyl group, a lower alkyl group, a substituted lower alkyl group having chlorine atom or hydroxyl group as substituent; or a lower alkenyl group.

2. 2-(2,4-Dimethylallophanoyl)-4-phenylpiperazine.

3. 1-(2,4,4-Trimethylallophanoyl)-4-(3-fluorophenyl)-piperzine.

4. 1-(2,4-Dimethylallophanoyl)-4-(3-trifluoromethylphenyl)piperazine.

5. 1-(2,4,4-Trimethylallophanoyl)-4-isopropylpiperazine hydrochloride.

6. 1-(2,4,4-Trimethylallophanoyl)-4-(3-trifluoromethylphenyl)piperazine.

7. 1-(2,4,4-Trimethylallophanoyl)-4-(4-chlorophenyl)piperazine.

8. 1-(2,4,4-Trimethylallophanoyl)-4-(3-nitrophenyl)piperazine.

9. 1-(2,4,4-Trimethylallophanoyl)-4-phenylpiperazine.

10. 1-(2,4,4-Trimethylallophanoyl)-4-(3,4-dichlorophenyl)piperazine.

11. 1-(2,4,4-Trimethylallophanoyl)-4-(4-fluorophenyl)piperazine.

12. 1-(2,4,4-Trimethylallophanoyl)-4-(4-bromophenyl)piperazine.

13. 1-(2,4,4-Trimethylallophanoyl)-4-(3-methoxyphenyl)piperazine.

14. 1-(2,4,4-Trimethylallophanoyl)-4-(4-carboxyphenyl)piperazine.

15. 1-(2,4,4-Trimethylallophanoyl)-4-(4-chloro-3-trifluoromethylphenyl)piperazine.

16. 1-(2,4,4-Trimethylallophanoyl)-4-(3,4-dimethoxyphenyl)piperazine.

17. 1-(2,4,4-Trimethylallophanoyl)-4-(3,4-methylenedioxyphenyl)piperazine.

18. 1-(2,4,4-Trimethylallophanoyl)-4-cyclohexylpiperazine.

19. 1-(2,4,4-Trimethylallophanoyl)-4-methylpiperazine.

20. 1-(2,4,4-Trimethylallophanoyl)-4-(β-hydroxyethyl)piperazine.

21. An analgesic composition containing as active ingredient an allophanylpiperazine compound represented by the general formula (1)

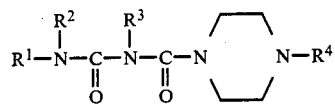  (1)

wherein $R^1$ represents a lower alkyl group or phenyl group; $R^2$ represents a lower alkly group; $R^3$ represents a lower alkyl group; and $R^4$ represents phenyl group or a substituted phenyl group having as substituent a halogen atom or methyl, trifluoromethyl, hydroxyl, methoxy, methylenedioxy, nitro or carboxyl group; pyridyl group, pyrimidyl group, thiazolyl group, benzyl group, cinnamyl group, cyclohexyl group, a lower alkyl group, a substituted lower alkyl group having chlorine atom or hydroxyl group as substituent; or a lower alkenyl group.

22. A method of inducing analgesia in a patient in need of such treatment comprising administering an analgesically effective amount of a compound represented by the general formula

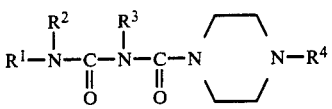

wherein $R^1$ represents a lower alkyl group or phenyl group; $R^3$ and $R^3$ each represents a hydrogen atom or a lower alkyl group; and $R^4$ represents phenyl group or a substituted phenyl group having as substituent a halogen atom or methyl, trifluoromethyl, hydroxyl, methoxy, methylenedioxy, nitro or carboxyl group; pyridyl group; pyrimidyl group, thiazolyl group, benzyl group, cinnamyl group, cyclohexyl group, a lower alkyl group, a substituted lower alkyl group having chlorine atom or hydroxyl group as substituent; or a lower alkenyl group to said patient.

* * * * *